United States Patent [19]

Counsell et al.

[11] Patent Number: 4,933,157
[45] Date of Patent: Jun. 12, 1990

[54] RADIOIODINATED ARYLALIPHATIC ETHER ANALOGUES OF CHOLESTEROL

[75] Inventors: Raymond E. Counsell; Mohamed K. Ruyan; Susan W. Schwendner; Laura E. Deforge, all of Ann Arbor, Mich.

[73] Assignee: The University of Michigan, Ann Arbor, Mich.

[21] Appl. No.: 212,196

[22] Filed: Jun. 27, 1988

[51] Int. Cl.$^5$ .......................... A61K 49/02; C07J 9/00
[52] U.S. Cl. ...................................... 424/1.1; 552/544
[58] Field of Search ...................... 424/1.1; 260/397.2

[56] References Cited

U.S. PATENT DOCUMENTS 3,784,576  1/1974  Counsell ............................. 424/1.1
4,430,321  2/1984  Flanagan et al. .................... 424/1.1

FOREIGN PATENT DOCUMENTS 2409971  9/1974  Fed. Rep. of Germany ... 260/397.2
0251141  11/1987  Fed. Rep. of Germany ... 260/397.2
1189294  8/1986  Japan ................................ 260/397.2

OTHER PUBLICATIONS

Sarma et al., "Cleavages of Ethers by Chorotrimethylsilane & Acetic Anhydride", Tetrahedron, vol. 42, No. 14, pp. 3999–4006, 1986.
Counsell et al., Tumor Localizing Agents, IX. Radioiodinated Cholesterol, *Steroids*, 16:317–328, (1970).
Kojima et al., *J. Nuclear Med.*, vol. 16, No. 7, p. 666, (1975).
Basmadjian et al., *J. Labelled Compounds*, vol. XI, No. 3, p. 427, (1975).
Maeda et al., *Steroids*, vol. 26, No. 2, p. 241, (1975).
Bosisio et al., *J. Steroid Biochemistry*, vol. 11, pp. 1113 to 1119, (1979).

Primary Examiner—John S. Maples
Attorney, Agent, or Firm—Rohm & Monsanto

[57] ABSTRACT

Novel radioiodinated analogues of naturally-occurring cholestrol esters, arylaliphatic cholesteryl ethers, are selective for low density lipoproteins and have been shown to be successful imaging agents for adrenal glands. The arylaliphatic cholesteryl ethers have the general formula:

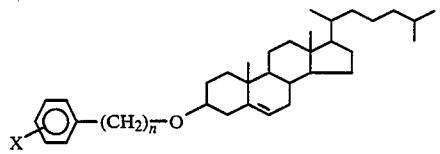

where X is a radioactive isotope of iodine and n is an integer between 1 and 20. Two illustrative examples, m-iodobenzyl cholesteryl ether and 12-(m-iodophenyl) dodecyl cholesteryl ether, were radiolabeled with $^{125}I$ by an isotope exchange reaction. Tissue distribution studies indicate significant accumulation of the cholesteryl ethers in the adrenal glands, and to a lesser extent in the liver. The cholesteryl ethers selectively incorporate into plasma lipoproteins as determined by polyacrylamide gel electrophoresis.

7 Claims, 3 Drawing Sheets

SCHEME 1
SYNTHESIS OF 12-(m-IODOPHENYL)-DODECYL METHANE SULFONATE

RADIOIODINATED ARYLALIPHATIC ETHER ANALOGUES OF CHOLESTEROL

This invention was made with government support under Grant Number CA-08349 awarded by the National Institutes of Health, the National Cancer Institute. The government has certain rights in the invention.

BACKGROUND OF THE INVENTION

1. Field of the Invention

This invention relates generally to radioiodinated compounds which are useful as radiopharmaceuticals, and more specifically, to radioiodinated arylaliphatic cholesteryl ether analogues of naturally-occurring cholesteryl esters which exhibit specificity for low density lipoproteins and are useful, inter alia, for scintigraphic imaging of adrenal glands and as biological probes for lipoprotein research.

2. Prior Art

Since the ester linkage of naturally-occurring cholesteryl esters is quickly hydrolyzed in vivo, cholesteryl ester analogues which are resistant to hydrolysis upon administration to animals or humans would be of significant value to researchers in quantitating cholesteryl ester uptake into tissues. Currently available cholesteryl ether compounds which are marketed for research purposes are radio-tagged with tritium ($^3$H). However, tritium emissions are of the weak beta type. In fact, the emission is so weak that tissue samples, for example, must be concentrated in vitro to faciliate detection. Equipment for detecting beta emission is required to be highly sensitive, and therefore costly. Thus, the use of beta-emissive marker compounds is problematical, even in a laboratory situation. For in vitro work, the gamma-emitting isotopes of iodine, particularly $^{125}$I, are the isotopes of choice.

The use of tritiated agents in in vivo applications has the further disadvantage that any intersecting structure, such as adjacent tissue, will completely absorb, or substantially mask, the emission before the tritium can be detected. Radiolabelling cholesteryl ester analogues with the gamma-emitting isotopes of iodine (particularly, $^{123}$I and $^{131}$I could be used to produce potentially useful scintigraphic imaging agents. There are currently available no radioiodinated analogues of naturally-occurring cholesteryl esters. Of particular interest would be scintigraphic agents which would be useful for detecting problems associated with, inter alia, coronary artery disease, adrenal dysfunction, and cancerous tumors.

Radioiodinated cholesterol analogues are currently in use for adrenal imaging. One known compound, a free norcholesterol, is marketed under the designation NP-59. NP-59 is chemically named 6-b-iodomethyl-19-norcholest-5[10]en-3b-ol, the uptake of which into the adrenal glands is extremely slow. In fact, it takes about five days to image the adrenal glands following administration of the imaging agent. Therefore, NP-59 is radiolabelled with $^{131}$I due to its long half-life. Thus, the radiation dose to the subject is high. Moreover, NP-59 is subject to metabolic loss of iodine and resulting accumulation of this iodine in the thyroid. There is, thus, a great need for a radiologic agent which is stable, non-metabolizable, inexpensive to produce and which can be administered to the subject with a low dosage of radioactivity.

There is additionally a need for a marker for low density lipoproteins (LDL). Low density lipoproteins are a cause atherosclerosis. There are not currently available any imaging agents for visualizing atherosclerotic lesions in vivo. Thus, a compound which can be radiolabelled and would be selectively localized in low density lipoproteins would be useful in the detection of coronary artery disease.

It is, therefore, an object of this invention to provide a radiopharmaceutical for gamma camera scintigraphy.

It is another object of this invention to provide a radio-pharmaceutical for selective visualization of, inter alia, adrenal glands, endocrine tumors, and atherosclerotic lesions.

It is also an object of this invention to provide a radiopharmaceutical which represents an improvement in terms of dosage requirement and rapidity of uptake over currently available agents.

It is a further object of this invention to provide radioiodinated analogues of naturally-occurring cholesteryl esters which are non-hydrolyzable upon administration to a human or animal.

It is additionally an object of this invention to provide radioiodinated arylaliphatic cholesteryl ether analogues of naturally-occurring cholesteryl esters which exhibit specificity for low density lipoproteins.

It is yet further object of this invention to provide a radioiodinated arylaliphatic cholesteryl ether analogues of naturally-occurring cholesteryl esters which are stable, non-metabolizable, inexpensive to produce, and which can be administered to the subject with a low dosage of radioactivity.

SUMMARY OF THE INVENTION

The foregoing and other objects are achieved by this invention which provides radioiodinated arylaliphatic cholesteryl ether analogues of naturally-occurring cholesteryl ester compounds of the general formula:

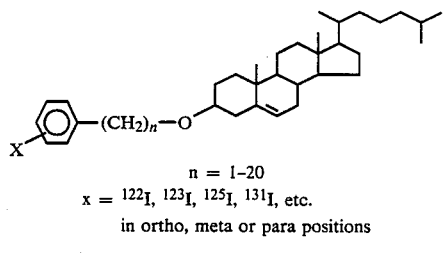

n = 1-20
x = $^{122}$I, $^{123}$I, $^{125}$I, $^{131}$I, etc.
in ortho, meta or para positions where X is a radioactive isotope of iodine in the ortho-, meta- or para-position. In certain embodiments of the invention, these isotopes may include $^{122}$I, $^{123}$I, $^{125}$I, and $^{131}$I, and n is an integer between 1 and 20.

In accordance with a method aspect of the invention, a physiologically effective amount of the inventive compound is administered to the body of a living being.

In accordance with an inventive use aspect of the invention, the compound having the general formula set forth hereinabove is utilized as a radiopharmaceutical for various imaging modalities. In an illustrative embodiment, the radioisotope of iodine is selected from the group of $^{122}$I, $^{123}$I, $^{125}$I, and $^{131}$I. An effective amount of the radioactive tracer compound is administered to the body of the living being so as to cause sufficient gamma rays to be emitted for imaging of adrenal glands by gamma-camera scintigraphy.

In accordance with a specific illustrative embodiment of the invention, the inventive compound is m-iodobenzyl cholesteryl ether.

In accordance with a still further specific illustrative embodiment of the invention, the inventive compound is 12-(m-iodophenyl)dodecyl cholesteryl ether.

BRIEF DESCRIPTION OF THE DRAWING

Comprehension of the invention is facilitated by reading the following detailed description in conjunction with the annexed drawing, in which.

DETAILED DESCRIPTION

The radioiodinated agents of this invention are non-metabolizable and stable. Since the radioactive iodine is attached to an aromatic ring, it is resistant to in vivo deiodination. Thus, uptake into the thyroid is minimal. Tissue distribution studies, as reported hereinbelow, show that only a very low percentage of iodine is taken into the thyroid following administration of the novel agents.

Researchers have previously used cholesteryl esters as a probe for lipoproteins but their studies have been hampered because the ester linkage is quickly cleaved. However, the novel cholesteryl ether analogues of the instant invention are taken into plasma lipoproteins more rapidly than the ester analogues and are highly selective for low density lipoproteins.

The following specific examples of embodiments of the invention are also illustrative of methods for synthesizing the radioiodinated arylaliphatic cholesteryl ether analogues of the present invention:

EXAMPLE 1

Preparation of m-Iodobenzyl Cholesteryl Ether

Figure 1:
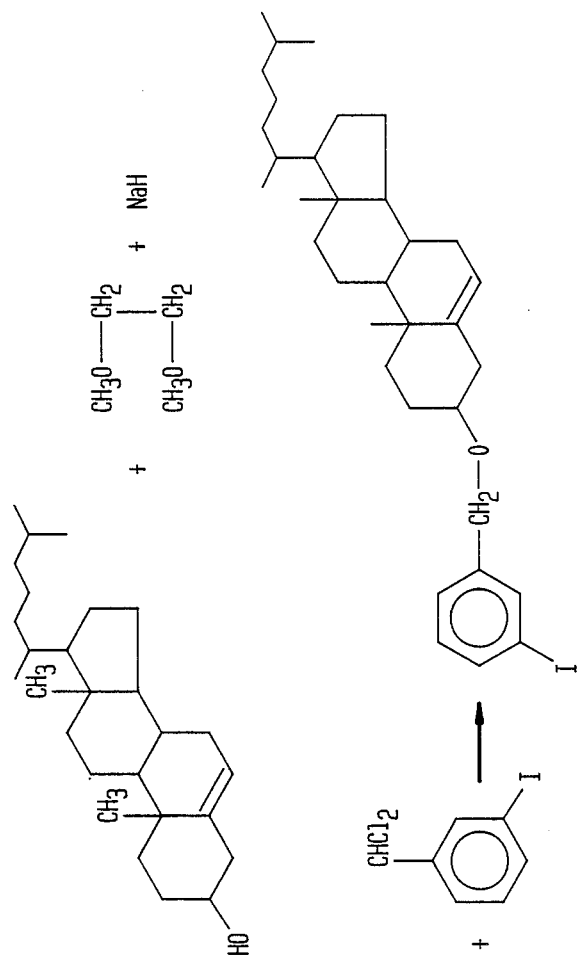
FIG. 1 is an illustrative preparatory scheme for m-iodobenzyl cholesteryl ether.

In a specific illustrative embodiment of a cholesteryl ether analogue in accordance with the present invention, the synthesis of m-iodobenzyl cholesteryl ether was accomplished in accordance with the illustrative preparatory scheme shown in FIG. 1.

Referring to FIG. 1, the preparation of m-iodobenzyl cholesteryl ether is described in detail. Cholesterol (568 mg, 1.98 mmol), anhydrous dimethoxyethane (8.0 ml), and NaH (140 mg, 15.8 mmol) were combined in a flame-dried, nitrogen flushed round-bottom flask which was fitted with a reflux condenser. The resulting mixture was stirred for 5 minutes at room temperature before m-iodobenzyl chloride (550 mg, 1.98 mmol) was slowly added with continued stirring. The reaction mixture was refluxed for 6 hours. After the reaction mixture had cooled to room temperature, H$_2$O (20 ml) was added. The organic layer was extracted with ether (20 ml, 3X). The ether extracts were dried over MgSO$_4$ and the solvent was removed under reduced pressure. The resulting solid residue was dissolved in benzene-hexane (3:7 and purified on a chormatography column of silica gel (53 g silica; benzene-hexane 3:7) to yield m-iodobenzyl cholesteryl ether as a white solid. The m-iodobenzyl cholesteryl ether was recrystallized from acetone (472 mg, 40%, mp 95°–96° C.).

EXAMPLE 2

Preparation of 12-(m-Iodophenyl) Dodecyl Cholesteryl Ether

Figure 2:
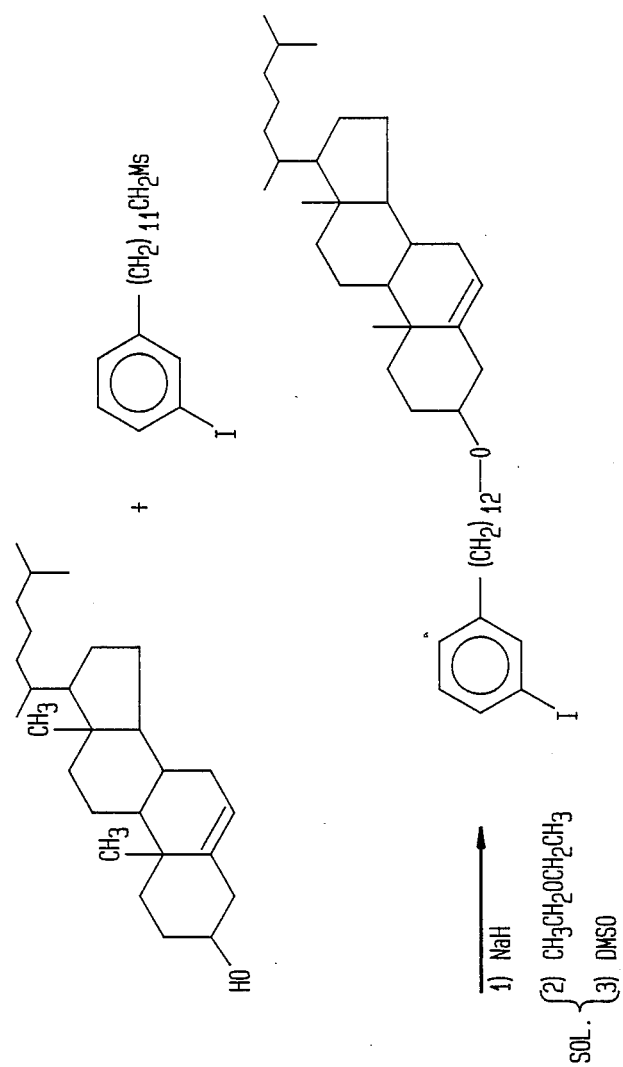
FIG. 2 is an illustrative preparatory scheme for 12-(m-iodophenyl)dodecyl cholesteryl ether.

In another specific illustrative embodiment of the invention, 12-(m-iodophenyl) dodecyl cholesteryl ether was synthesized in accordance with the reaction scheme shown in FIG. 2.

Figure 3:
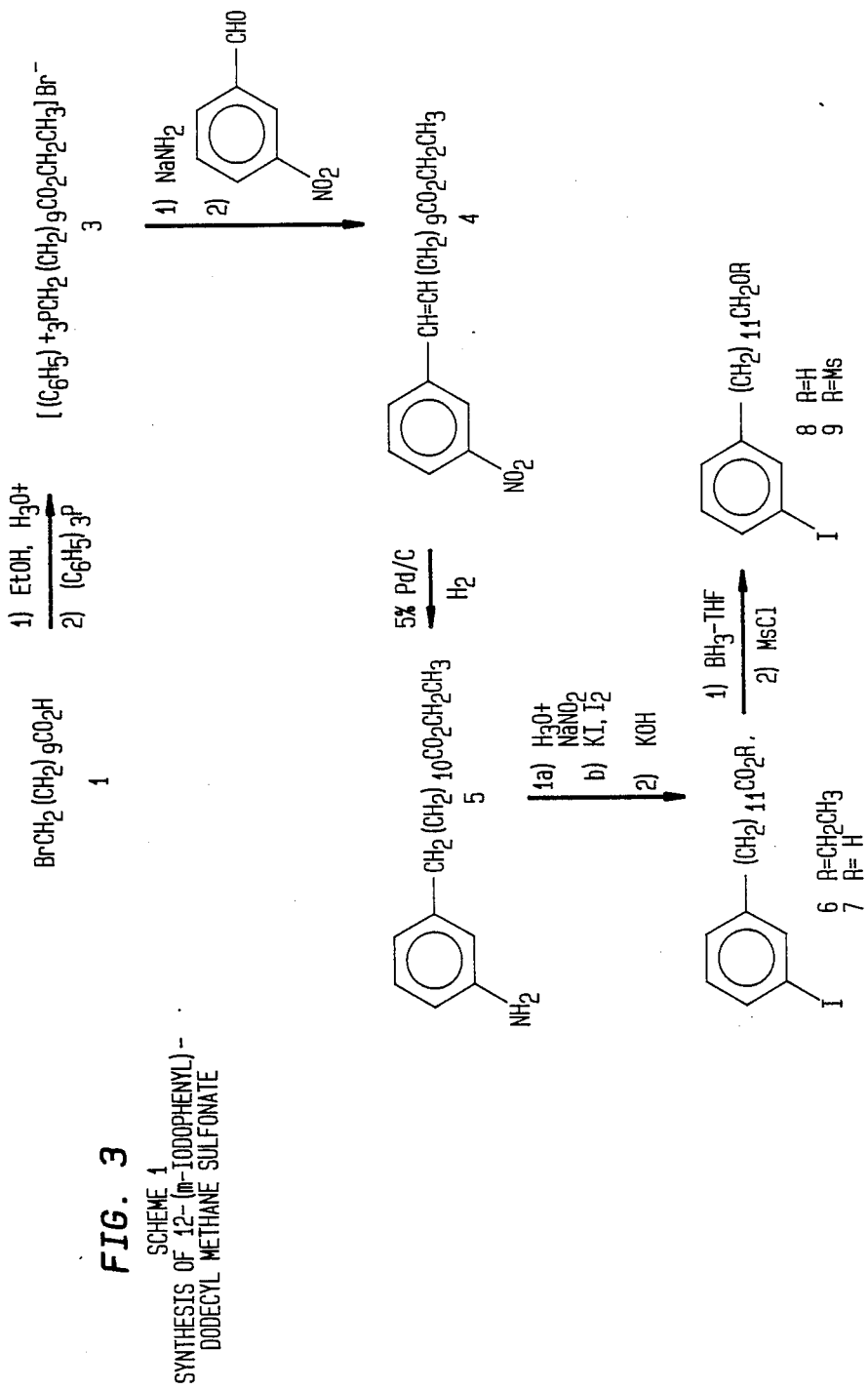
FIG. 3 is an illustrative preparatory scheme for 12-(m-iodophenyl)dodecyl methane sulfonate.

The synthesis of 12-(m-iodophenyl)-dodecyl methane sulfonate, a necessary compound in the illustrative preparatory scheme for the cholesteryl ether analogue of this Example 2 was synthesized from 11-bromoundecanoic acid in accordance with an illustrative preparatory scheme shown in FIG. 3. This technique is also described in detail in a copending application Ser. No. 112,865, filed Oct. 23, 1987 and assigned to the assignee hereof.

In general terms, the preparatory scheme for 12-(m-iodophenyl)dodecyl methane sulfonate shown in FIG. 3 comprises: esterification of 11-bromoundecanoic acid (compound 1) followed by reaction with triphenylphosphine to yield the corresponding phosphonium salt (compound 3). A Wittig reaction involving compound 3 with m-nitrobenzaldehyde afforded m-nitrophenyl alkenoate (compound 4) which, upon subsequent catalytic hydrogenation gave rise to an m-aminophenyl alkanoate (compound 5). The m-aminophenyl alkanoate was converted to the corresponding diazonium salt and the diazonium ion was subsequently displaced by iodide to afford the iodinated ester (compound 6). The ester was saponified to give the corresponding acid (compound 7). The acid was reduced to the alcohol (compound 8) which was mesylated to form the mesylate (compound 9).

Compound 1, 11-Bromoundecanoic acid (41.38 g, 156 mmol), was placed in a 250 ml round-bottomed flask equipped with a reflux condenser. After absolute ethanol (60 ml) and concentrated HCl (½ ml) were added, the reaction mixture was refluxed overnight. The reaction mixture was allowed to cool to room temperature before the solvent was removed under reduced pressure. The resulting yellow oil was dissolved in ether. The ether solution was extracted with saturated NaHCO$_3$ and H$_2$O, and dried over MgSO$_4$. The solvent was removed under reduced pressure. Purification of the crude product was obtained by vacuum distillation which yielded a colorless oil, ethyl-11-bromoundecanoate, compound 2 (37.32 g, 82.5% yield).

Ethyl-11-bromoundecanoate (36.0 g, 123 mmol) and acetonitrile (200 ml) were placed in a flame-dried three-neck 500 ml round-bottomed flask equipped with a reflux condenser. Triphenyl phosphine (35.5 g, 135 mmol) was added to the solution and the reaction mixture was refluxed for 36 hours under anhydrous conditions. After the reaction mixture had cooled to room temperature, the acetonitrile was removed under reduced pressure. The crude product was triturated with ether. The solid was filtered and washed with ether to yield a pure compound 3, 11-carbethoxyundecyltriphenylphosphonium bromide (56.69 g, 83% yield).

Sodium amide (0.40 g, 9.74 mmol) was weighed directly into a flame-dried 50 ml round-bottomed flask filled with Argon. 11-Carbethoxyundecyltriphenylphosphonium bromide (5.00 g, 9.0 mmol was added. The mixture was cooled to $-30°$ C. After the reaction mixture had stirred for 30 minutes at $-30°$ C., a solution of m-nitrobenzaldehyde (1.4 g, 9.30 mmol) in anhydrous tetrahydrofuran (THF, 2 ml) was added drop-wise. The reaction mixture was allowed to warm to room temperature and was stirred for 4 hours. Ether was added. The reaction mixture was cooled to 0° C. and $H_2O$ was cautiously added to destroy residual base. The ether layer was removed, washed with $H_2O$, 2% $NaHSO_4$ and brine, and dried ($MgSO_4$). The solvent was evaporated under reduced pressure to yield an oily residue. Purification by column chromatography (150 g silica gel, hexane:ethyl acetate, 15:1) gave the pure compound 4, ethyl-12-(m-nitrophenyl)-11-dodecenoate (1.323 g, 42% yield).

Ethyl-12-(m-nitrophenyl-11-dodecanote (9.76 g, 28.1 mmol) was dissolved in ethyl acetate (55 ml). The solution was hydrogenated over 5% Pd/C (0.346 g) at room temperature and at an initial pressure of 45 psi for four hours. The reaction mixture was filtered through Celite and the solvent was removed under reduced pressure to yield an oily residue. The crude product was purified by column chromatography (80 g silica gel, hexanes:ethyl acetate, discontinuous gradient 10:1–2:1) to yield the reduced compound 5, ethyl-12-(m-aminophenyl)-dodecanoate (8.75 g, 97.5% yield).

Glacial acetic acid (4 ml) and concentrated HCl (2.5 ml) were added to a 50 ml Erlenmeyer flask containing ethyl-12-(m-aminophenyl)-dodecanoate (3.92 g, 12.28 mmol). The mixture was cooled in a NaCl/ice bath. A cold aqueous solution of $NaNO_2$ (4 ml, 3.1M) was added to the mixture. The reaction was stirred for 40 minutes before a cold aqueous solution of $KI/I_2$ (2.31 g/1.78 g, 7 ml $H_2O$) was added. The reaction mixture was allowed to warm to room temperature and was stirred overnight. Ether was added to the reaction mixture. The ether layer was separated and extracted with $H_2O$, 10% $Na_2S_2O_3$, $H_2O$, sat. $NaHCO_3$, and brine. The organic layer was dried ($MgSO_4$) and the solvent removed under reduced pressure to give a reddish oil. The crude product was purified by column chromatography (120 g silica gel, hexanes:-ethyl acetate 20:1) to yield a clear oil, compound 6, ethyl-12-(m-iodophenyl)-dodecanoate (5.28 g, 56.8% yield).

Ethyl-12-(m-iodophenyl)-dodecanoate (7.17 g, 16.67 mmol), 95% ethanol (100 ml) and KOH (2.0 g) were placed into a 250 ml round-bottomed flask fitted with a reflux condenser. The reaction mixture was refluxed overnight. The ethanol was removed in vacuo and $H_2O$ was added. The aqueous solution was acidified and then extracted with ether. The ether layer was dried ($MgSO_4$), and the solvent was evaporated to yield a yellow solid. The crude product was recrystallized with 95% ethanol to provide a white flaky solid, compound 7, 12-m-iodophenyldodecanoic acid (5.9 g, 88.0% yield).

Anhydrous THF (20 ml) was added to a flame-dried 100 ml two-necked flask containing 12-m-iodophenyl-dodecanoic acid (3.30 g, 8.21 mmol). The solution was cooled in an ice bath before $BH_3$-THF (15.0 ml, 1M) was added drop-wise. The reaction mixture was allowed to warm to room temperature and to stir under anhydrous conditions for 20 hours. The reaction mixture was again cooled to 0° C. and quenched with $H_2O$. Ether and additional $H_2O$ were then added. The ether layer was extracted with $H_2O$, sat. $NaHCO_3$, and more $H_2O$ and dried ($MgSO_4$). The solvent was removed under reduced pressure to yield a yellow oil. The crude compound was purified by column chromatography (90 g silica gel, hexanes-:ethyl acetate 8:1) to yield a white solid, compound 8, 12-m-iodophenyldodecanol (3.14 g, 98.4% yield).

12-m-Iodophenyldodecanol (5.88 g, 15.17 mmol) was placed into a flame-dried three-neck 100 ml round-bottomed flask equipped with a reflux condenser and charged with $N_2$. Anhydrous pyridine (30 ml) was added. The mixture was cooled to 0° C. before freshly distilled methanesulfonyl chloride (2.0 ml, 25.96 mmol) was added drop-wise. The reaction mixture was allowed to warm to room temperature. After the reaction mixture had been stirred for several hours, it was poured into ice cold $H_2O$ and the resulting precipitate was filtered. The solid was dissolved in ether and extracted with $H_2O$, 1N HCl, and $H_2O$. The ether layer was dried (MgSO4) and the solvent was evaporated in vacuo. The crude product was recyrstallized with a hexanes and ethyl acetate mixture to yield the pure mesylate, compound 9, 12-(m-iodophenyl)dodecyl methane sulfonate (4.95 g, 70.7%).

Referring now to FIG. 2, etherification of cholesterol with 12-(m-iodophenyl)dodecyl methane sulfonate results in the desired product, 12-(m-iodophenyl)dodecyl cholesteryl ether.

Cholesterol (500 mg, 1.29 mmol) was dissolved in ethyl ether (5 ml) and dimethylsulfoxide (DMSO; 2 ml). NaH (40 mg, 1.33 mmoles) was carefully added to the cholesterol solution, under anhydrous conditions, at room temperature. This mixture was stirred for about 5 minutes. A mixture of 12-(m-iodophenyl)-dodecyl methane sulfonate (400 mg, 0.86 mmoles) in ether (5 ml) was then added drop-wise to the cholesterol mixture over a period of about 5 minutes. This reaction mixture was heated to 40° C. for 10 hours until thin layer chromatography indicated the absence of 12-(m-iodophenyl)dodecyl methane sulfonate and the presence of the cholesterol ether ($R_f$=0.6).

The reaction mixture was added to a separatory funnel containing $H_2O$ (50 ml) and extracted with ether (50 ml; 3X). The ether fraction was dried over $MgSO_4$ and the solvent was removed under pressure to yield a white solid. The white solid was dissolved in benzene-hexane 3:7 (5 ml) and purified on a silica gel chromatography column (10 g; benzene-hexane 3:7). Following removal of the solvent from the product-containing fraction, a residual oil, which was dried overnight in vacuo, comprised the desired ether, 12-(m-iodophenyl)-dodecyl cholesteryl ether (216 mg, 33.2% yield).

Radioiodination of the Cholesteryl Ether Analogues

Radioiodination of the iodinated arylaliphatic ether analogues disclosed herein, or one of the intermediates in the synthesis pathway, such as a trityl-protected compound, can be accomplished by a variety of techniques, some of which are known in the art. For example, aromatic compounds with electron donating groups (such as anilines) can be radiolabelled by electrophilic iodination in the presence of radioiodine, iodine monochloride, chloramine-T, iodogen, etc. Unactivated aromatic rings, can be radioiodinated by exchange of a leaving group, such as aryl boronic acids, aryl thallium trifluoroacetates, triazenes or metallated arenes with radioiodine. Direct electrophilic radioiodination of a phenyl ring is yet another alternative, but may give rise to isomeric mixtures which are difficult to separate. Iodine exchange of aryl iodides with radioiodine may be a preferable approach insofar as no complex separation techniques are necessary since the substrate and radioiodinated product are chemically identical.

In a preferred embodiment of the invention, an isotope exchange-type technique is utilized wherein the substrate and radioiodine are reacted at an elevated temperature in a "melt." The molten reaction medium possesses a sufficiently high dielectric constant to solubilize both the substrate and radioiodide. Examples of reaction media currently in use are benzoic acid (mp 122° C., bp 249° C.) and acetamide (mp 82° C., bp 221° C.). In a specific preferred embodiment, an acidic exchange medium comprising pivalic acid, a homolog of acetic acid, also known as trimethyl acetic acid, was used. Pivalic acid has a melting point of 33° C. and a boiling point of 164° C.

The cholesteryl ether compound (1 mg) and pivalic acid (10 mg) were placed in a 1 ml serum vial. The vial was flushed with $N_2$ and sealed with a teflon-lined rubber septum and aluminum cap. Aqueous $Na^{125}I$ (0.5–1.0 $\mu L$, 100–500 $\mu Ci$) was added. A stream of $N_2$ was used to remove the water and the reaction mixture was then heated at 150° C. for 30 minutes. The reaction mixture was allowed to cool to room temperature before extraction with a chloroform:methanol mixture (1:2 volume ratio, 60 $\mu L$) and water (60 $\mu L$) were added. The organic layer was removed and added to a silica gel-60 column (1×5 cm). The column was initially eluted with chloroform:methanol (1:1) to remove the $Na^{125}I$ and then with chloroform:methanol:water (65:25:4) to obtain the radioiodinated product.

In another specifically advantageous embodiment of the invention, the novel radioiodinated arylaliphatic cholesteryl ether analogues can be radiolabelled by the following technique:

A mixture of copper sulfate (200 $\mu g$), ascorbic acid (5 mg), and the arylaliphatic cholesteryl ether analogue (2 mg) was placed in a small vial and dissolved in 1,3-Dimethyl-3,4,5,6-tetrahydro-2(1H)-pyrimidinone (12 $\mu l$). The sodium salt of the desired iodine isotope, illustratively 1 mCi $Na^{125}I$, was added to the vial and the entire mixture was heated for about ½ hour at 160° C. The product was purified on a silica gel column and eluted with 5% ethyl acetate in hexane to obtain the radioiodinated product. HPLC was used to insure the purity of the product. This technique resulted in a greater than 90% yield of radioiodinated product.

Of course, any isotope of iodine such as the clinically used isotopes, $^{122}I$, $^{123}I$, $^{125}I$ and $^{131}I$, can be used. $^{125}I$ is preferred for in vitro work in the laboratory due to its relatively long half-life. For radiodiagnostic purposes in humans, $^{123}I$ or $^{131}I$ is preferred due to their shorter half-lives. The advent of positron emission tomography has also created a use for the positron-emitting $^{122}I$ isotope. The radioiodination procedures may be modified, as known by those of skill in the art, to compensate for the difference in half-life.

The above-described radioiodinated arylaliphatic cholesteryl ether analogues may be solubilized in a suitable transport agent, or carrier vehicle, and administered to mammalian subjects as radiologic agents by any known manner, preferably intraparentally such as intravenously or intraperitoneally.

EXPERIMENTAL RESULTS

1. Tissue Distribution Studies

Radiolabelled compounds, m-iodobenzyl cholesteryl ether (Example 1) and 12-(m-iodophenyl)dodecyl cholesteryl ether (Example 2) were prepared and administered to female Sprague Dawley rats. The labelled compounds (5–35 mCi $^{125}I$) were administered intravenously in a 2% Tween-20-saline vehicle. At various times following administration, the animals were sacrificed, and selected tissue samples were removed. The tissue samples were weighed and placed in cellulose acetate capsules. The radioactivity was then counted (85%) efficiency using a well scintillation counter (Searle 1185). The results from selected tissue samples are shown below in Tables 1 and 2. The tissue distribution of the selected cholesteryl ether is expressed as percent Kg dose per g of tissue after 30 minutes (Table 1) and after 24 hours (Table 2).

TABLE 1

TISSUE DISTRIBUTION OF RADIOACTIVITY AT 30 MINUTES FOLLOWING IV ADMINISTRATION OF RADIOIODINATED-CHOLESTERYL ETHERS TO FEMALE RATS (% KG DOSE/G OF TISSUE)

| Tissue | m-Iodobenzyl | m-Iodophenyldodecyl |
|---|---|---|
| Adrenal | 1.347 ± 0.289 | 1.307 ± 0.177 |
| Blood | 0.985 ± 0.127 | 1.250 ± 0.067 |
| Liver | 1.414 ± 0.176 | 0.829 ± 0.121 |
| Ovary | 0.635 ± 0.036 | 0.936 ± 0.136 |
| Thyroid | 0.133 ± 0.018 | 0.486 ± 0.085 |

TABLE 2

TISSUE DISTRIBUTION OF RADIOACTIVITY AT 24 HOURS FOLLOWING IV ADMINISTRATION OF RADIOIODINATED CHOLESTERYL ETHERS TO FEMALE RATS (% KG DOSE/G OF TISSUE)

| Tissue | m-Iodobenzyl | m-Iodophenyldodecyl |
|---|---|---|
| Adrenal | 3.755 ± 0.362 | 3.063 ± 0.305 |
| Blood | 0.070 ± 0.006 | 0.085 ± 0.002 |
| Liver | 2.607 ± 0.072 | 1.779 ± 0.247 |
| Ovary | 1.924 ± 0.301 | 4.528 ± 0.816 |
| Thyroid | 1.307 ± 0.150 | 6.047 ± 0.760 |

At 30 minutes, there is still a significant amount of radioactivity in the blood. However, the selectivity for the adrenal glands is demonstrated. Since the liver has a high percent of lipoprotein receptors, the radioiodinated cholesteryl ether analogues of the invention will also localize in the liver. At 24 hours, there is approximately fifty times more activity in the adrenal tissue than in the blood. There is also significantly more activity in the adrenal tissue than in the liver tissue. The data indicates that these agents may also be useful for imaging ovarian tissue.

Therefore, the novel compounds of the instant invention are particularly useful for imaging adrenal glands. In a specific advantageous embodiment, the adrenal glands can be suppressed by administering a glucocorticoid, such as prednisone, to inhibit the uptake of lipoproteins. However, tumors which are not so easily subject to suppression by administration of a glucocorticoid, will continue to take up lipoproteins, and therefore, be clearly imaged through use of the lipoprotein-specific agents of the present invention.

The data reported in Table 3 demonstrates that the same type of tissue distribution, i.e., high concentration in adrenal and liver tissue, occurs upon administration of the radioiodinated cholesteryl ether analogues to male Hartley guinea pigs. The tissue distribution of m-iodobenzyl cholesteryl ether is expressed as percent Kg dose per g of tissue after 30 minutes and after 24 hours.

TABLE 3
TISSUE DISTRIBUTION OF RADIOACTIVITY
FOLLOWING IV ADMINISTRATION OF
RADIOIODINATED M-IODOBENZYL CHOLESTERYL
ETHER TO MALE GUINEA PIGS
(% KG DOSE/G OF TISSUE)

| Tissue | 30 min | 24 hr |
|---|---|---|
| Adrenal | 0.360 ± 0.019 | 7.861 ± 0.656 |
| Blood | 0.799 ± 0.041 | 0.158 ± 0.020 |
| Liver | 0.643 ± 0.044 | 2.023 ± 0.147 |
| Testes | 0.025 ± 0.002 | 0.043 ± 0.010 |
| Thyroid | 0.039 ± 0.002 | 1.546 ± 0.279 |

2. Plasma Level Studies

Female Sprague Dawley rats were injected with a radio-iodinated arylaliphatic cholesteryl ether analogue ($^{125}$I) solubilized in a suitable transport agent, such as 2% Tween 20-saline. After a predetermined time period, blood samples were drawn from the rats. The plasma was separated from the red blood cells and mixed with a suitable dye (Sudan Black or Sudan Blue). The plasma samples were then subjected to polyacrylamide gel electrophoresis to separate the various fractions. The radioactivity of the various fractions were measured with a gamma counter. The results for rat plasma samples after 30 minutes and 24 hours are given below in Tables 4 and 5. The data is expressed as a percent of total radioactivity in the gel.

TABLE 4
POLYACRYLAMIDE GEL ELECTROPHORESIS
OF RAT PLASMA AT 30 MINUTES
(% OF TOTAL RADIOACTIVITY IN GEL)

| Gel Fraction | m-Iodobenzyl | m-Iodophenyldodecyl |
|---|---|---|
| Stacking Gel | 5.4 ± 2.5 | 21.6 ± 5.8 |
| LDL Band* | 41.0 ± 3.5 | 31.2 ± 4.0 |
| HDL Band** | 53.3 ± 2.2 | 45.7 ± 3.2 |
| Albumin | 0.3 ± 0.1 | 1.1 ± 0.2 |
| Below Alb | 0.0 ± 0.0 | 0.5 ± 0.1 |

*LDL = low density lipoproteins
**HDL = high density lipoproteins

TABLE 5
POLYACRYLAMIDE GEL ELECTROPHORESIS
OF RAT PLASMA AT 24 HOURS
(% OF TOTAL RADIOACTIVITY IN GEL)

| Gel Fraction | m-Iodobenzyl | m-Iodophenyldodecyl |
|---|---|---|
| Stacking Gel | 21.6 ± 5.8 | 11.6 ± 1.3 |
| LDL Band | 31.2 ± 4.0 | 14.0 ± 1.0 |
| HDL Band | 45.7 ± 3.2 | 66.2 ± 2.6 |
| Albumin | 1.1 ± 0.2 | 3.4 ± 0.7 |
| Below Alb | 0.5 ± 0.1 | 4.9 ± 1.3 |

After 30 minutes, 41% of the dose is observed in the low density lipoprotein fraction. This is surprising since rats do not have a high level of low density lipoproteins in their blood (10% LDL: 90% HDL).

Table 6 shows the results for guinea pig plasma samples after 30 minutes and 24 hours for m-iodobenzyl cholesteryl ether. Guinea pigs have a greater concentration of low density lipoproteins in their blood plasma than rats. The superior selectivity of the novel compounds for low density lipoproteins is clearly demonstrated inasmuch as greater than 70% of the dose is associated with the low density lipoproteins within 24 hours post-injection.

TABLE 6
POLYACRYLAMIDE GEL ELECTROPHORESIS
OF GUINEA PIG PLASMA FOLLOWING IV
ADMINISTRATION OF RADIOIODINATED
m-IODOBENZYL CHOLESTERYL ETHER
(% OF TOTAL RADIOACTIVITY IN GEL)

| Tissue | 30 min | 24 hr |
|---|---|---|
| Stacking Gel | 24.4 ± 7.4 | 13.4 ± 0.7 |
| VLDL Band | 28.6 ± 0.2 | 6.0 ± 0.5 |
| LDL Band | 32.5 ± 4.2 | 72.2 ± 2.0 |
| HDL Band | 11.5 ± 1.2 | 3.5 ± 1.2 |
| Albumin | 2.4 ± 0.8 | 2.7 ± 0.3 |
| Below Alb | 0.6 ± 0.2 | 2.2 ± 0.4 |

Although the invention has been described in terms of specific embodiments and applications, persons skilled in this art can, in light of this teaching, generate additional embodiments without exceeding the scope or departing from the spirit of the claimed invention. In particular, the methods of synthesis are merely illustrative and can be modified by those of skill in the art for the production of various arylaliphatic cholesteryl ether analogues in accordance with the invention. Moreover, other techniques for radio-tagging the analogues may be employed. Accordingly, it is to be understood that the drawings and descriptions in this disclosure are proffered to facilitate the comprehension of the invention and should not be construed to limit the scope thereof.

What is claimed is:

1. A compound of the general formula:

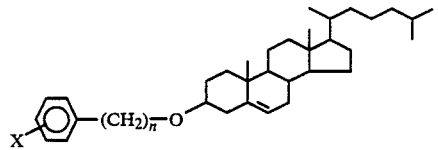

where X is a radioactive isotope of iodine and n is an integer between 1 and 20.

2. The compound of claim 1 wherein X is selected from the group of radioactive isotopes of iodine consisting of $^{122}$I, $^{123}$I, $^{125}$I, and $^{131}$I.

3. The compound of claim 1 wherein said compound is m-iodobenzyl cholesteryl ether.

4. The compound of claim 1 wherein said compound is 12-(m-iodophenyl)dodecyl cholesteryl ether.

5. A radiodiagnostic compound having the general formula:

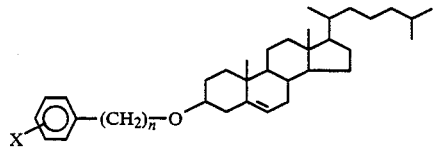

where X is a radioactive isotope of iodine and n is an integer between 1 and 20.

6. The compound of claim 5 wherein X is selected from the group of radioactive isotopes of iodine consisting of $^{122}$I, $^{123}$I, $^{125}$I, and $^{131}$I.

7. A method of radioimaging certain tissue of a living being comprising the steps of administering to the body of a living being a radiodiagnostic agent of claim 6 and subsequently observing radiation localized in the certain tissues of said living being.

* * * * *

UNITED STATES PATENT AND TRADEMARK OFFICE
CERTIFICATE OF CORRECTION

PATENT NO. : 4,933,157

DATED : June 12, 1990

INVENTOR(S) : Counsell, et al.

It is certified that error appears in the above-identified patent and that said Letters Patent is hereby corrected as shown below:

Column 1, between the title and the heading "Background of the Invention", please insert the following paragraph:

-- Government Rights

This invention was made with Government support under Grant No. CA08349 awarded by the National Institutes of Health. The Government has certain rights in the invention--.

Signed and Sealed this

Fifth Day of January, 1993

*Attest:*

DOUGLAS B. COMER

*Attesting Officer*   *Acting Commissioner of Patents and Trademarks*